(12) United States Patent
Yoon et al.

(10) Patent No.: US 11,730,606 B2
(45) Date of Patent: Aug. 22, 2023

(54) EXPANDABLE BI-DIMENSIONAL INTERBODY AND METHOD OF MANUFACTURING THE SAME

(71) Applicant: CTL Amedica Corporation, Addison, TX (US)

(72) Inventors: Hongwon Yoon, Allen, TX (US); Jon Suh, Ambler, PA (US); Sean Suh, Milltown, NJ (US)

(73) Assignee: CTL Biotec, Corporation

( * ) Notice: Subject to any disclaimer, the term of this patent is extended or adjusted under 35 U.S.C. 154(b) by 0 days.

(21) Appl. No.: 17/559,565

(22) Filed: Dec. 22, 2021

(65) Prior Publication Data

US 2023/0190489 A1 Jun. 22, 2023

(51) Int. Cl.
*A61F 2/44* (2006.01)
*A61F 2/46* (2006.01)
*A61F 2/30* (2006.01)

(52) U.S. Cl.
CPC .......... *A61F 2/4425* (2013.01); *A61F 2/4455* (2013.01); *A61F 2/4611* (2013.01); *A61F 2002/30179* (2013.01)

(58) Field of Classification Search
CPC .... A61F 2/4425; A61F 2/4455; A61F 2/4611; A61F 2002/30179
USPC ........................................... 623/17.11–17.16
See application file for complete search history.

(56) References Cited

U.S. PATENT DOCUMENTS

| | | | |
|---|---|---|---|
| 8,062,373 B2 | 11/2011 | Fabian, Jr. | |
| 9,079,550 B2 | 7/2015 | Fabian et al. | |
| 9,271,843 B2 | 3/2016 | Fabian et al. | |
| 9,421,113 B2 | 8/2016 | Fabian | |
| 2015/0335434 A1 | 11/2015 | Patterson et al. | |
| 2016/0296339 A1 | 10/2016 | De Villiers et al. | |
| 2017/0312092 A1 | 11/2017 | Link et al. | |
| 2019/0290448 A1 | 9/2019 | Predick et al. | |
| 2021/0128315 A1* | 5/2021 | Predick | A61F 2/4455 |
| 2021/0315712 A1 | 10/2021 | Sharifi et al. | |
| 2021/0322179 A1* | 10/2021 | Miller | A61F 2/447 |
| 2021/0386555 A1* | 12/2021 | Hessler | A61F 2/447 |

OTHER PUBLICATIONS

International Search Report dated Apr. 26, 2023 in counter part International Patent Application No. PCT/US2022/082093.
Written Opinion of the International Searching Authority dated Apr. 26, 2023 in counter part International Patent Application No. PCT/US2022/082093.

* cited by examiner

*Primary Examiner* — Eduardo C Robert
*Assistant Examiner* — Tara Rose E Carter
(74) *Attorney, Agent, or Firm* — Kim IP Law Group LLC

(57) ABSTRACT

An expandable bi-dimensional intervertebral implant for an intervertebral fusion is provided. The implant includes a first hinge arm, a second hinge arm connected to the first hinge arm, and a translation member movable relative to the first hinge arm and the second hinge arm between an initial position and an engaged position. The second hinge arm is movable between a primary position and a secondary position relative to the first hinge arm. In the engaged position, the translation member biases the first hinge arm to move from a first position to a second position and biases the second hinge arm to move between a first position and a second position.

20 Claims, 17 Drawing Sheets

EXPANDABLE BI-DIMENSIONAL INTERBODY AND METHOD OF MANUFACTURING THE SAME

BACKGROUND OF THE INVENTION

The subject disclosure relates generally to an implant and method for promoting an intervertebral fusion. In particular, the subject disclosure relates to an expandable bi-dimensional interbody capable of being inserted between adjacent vertebrae to facilitate interbody fusion of the spine.

A common procedure for handling pain associated with intravertebral discs that have become degenerated due to various factors such as trauma or aging is the use of intervertebral fusion devices for fusing one or more adjacent vertebral bodies. In order to fuse adjacent vertebral bodies, the intervertebral disc must be partially or fully removed. An intervertebral fusion device is then inserted between neighboring vertebrae to maintain normal disc spacing and restore spinal stability, thereby promoting intervertebral fusion.

Conventional fusion devices include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together to alleviate associated pain.

However, there are drawbacks associated with conventional fusion devices. For example, typical expandable fusion cages are made of multiple components with many intricate mating features. Such components are made from subtractive manufacturing which can be time consuming to machine each component individually and consequently becomes expensive. Moreover, solid fusion cages do not provide anterior/posterior translation and may be undersized or oversized during implantation causing expulsion, creating a less than ideal fit and a poor or delayed fusion result, and/or causing subsidence into an endplate of the vertebral body. As a result, inventories of different fixed cage heights are necessary. The above-mentioned factors result in higher market costs for implants along with slow turnaround times and dead inventory.

Thus, there is still a need for an interbody implant capable of being implanted inside an intervertebral disc space that addresses the aforementioned problems of conventional fusion devices. Such a need is satisfied by the expandable bi-dimensional interbody of the subject disclosure.

BRIEF SUMMARY

In accordance with an exemplary embodiment, the subject disclosure provides an expandable bi-dimensional intervertebral implant having a first hinge arm, a second hinge arm and a translation member movable relative to the first hinge arm and the second hinge arm between an initial position and an engaged position. The second hinge arm is connected to the first hinge arm and is movable between a primary position and a secondary position relative to the first hinge arm. In the engaged position, the translation member biases the first hinge arm to move from a first position to a second position and biases the second hinge arm to move between a first position and a second position.

In an aspect of the subject disclosure, the first hinge arm is a first bifurcated hinge arm having a first arm segment and a second arm segment. The first bifurcated hinge arm includes free ends movable between the first position and the second position. In the first position, the free ends of the first bifurcated hinge arms are spaced apart a first distance and in the second position, the free ends of the first bifurcated hinge arms are spaced apart a second distance greater than the first distance. The first hinge arm includes a locking tab for locking the first hinge arm and the second hinge arm in the secondary position. The first hinge arm includes a track engaging the translation member.

In accordance with another aspect of the subject disclosure, the second hinge arm is a second bifurcated hinge arm having a first arm segment and a second arm segment. The second bifurcated hinge arm includes free ends movable between the first position and the second position. In the first position, the free ends of the second bifurcated hinge arms are spaced apart a first distance and in the second position, the free ends of the first bifurcated hinge arms are spaced apart a second distance greater than the first distance. The translation member is positioned between the first and second arm segments of the first hinge arm. The translation member is positioned between the first and second arm segments of the second hinge arm.

In accordance with yet another aspect of the subject disclosure, the second hinge arm is hingedly connected to a mid-portion of the first hinge arm about its mid-portion. The translation member includes a translation element and a shaft operatively engaged with the translation element for moving the translation element between an initial position and an engaged position. The shaft is attached to the first hinge arm in a fixed axial position. The translation element includes a cam for engaging the first and second hinge arms.

In accordance with another exemplary embodiment, the subject disclosure provides an expandable bi-dimensional intervertebral implant having a first bifurcated hinge arm, a second bifurcated hinge arm hingedly connected to the first bifurcated hinge arm, and a translation member. The first bifurcated hinge arm includes a first arm segment and a second arm segment moveable relative to the first arm segment. The second bifurcated hinge arm includes a first arm segment and a second arm segment moveable relative to the first arm segment. The first bifurcated hinge arm and the second bifurcated hinge arm are movable between a primary position and a secondary position. The translation member is between the first and second arm segments of the first and second bifurcated hinge arms and movable relative to the first bifurcated hinge arm and the second bifurcated hinge arm between an initial position and an engaged position. In the engaged position, a posterior end of the expandable bi-dimensional intervertebral implant has a first height and an anterior end of the expandable bi-dimensional intervertebral implant has a second height greater than the first height. In the engaged position, the translation member splays first and second bifurcated hinge arms.

The subject disclosure further provides a method of manufacturing an expandable bi-dimensional intervertebral implant having the step of additively manufacturing the expandable bi-dimensional intervertebral implant of the subject disclosure as a fully assembled component. Each component of the expandable bi-dimensional intervertebral implant is additively manufactured with successive layers of material substantially parallel to a superior face of the first hinge arm.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the exemplary embodiments of the subject disclosure are not limited to the precise arrangements and instrumentalities shown.

In the drawings.

DETAILED DESCRIPTION OF THE INVENTION

Figure 1:
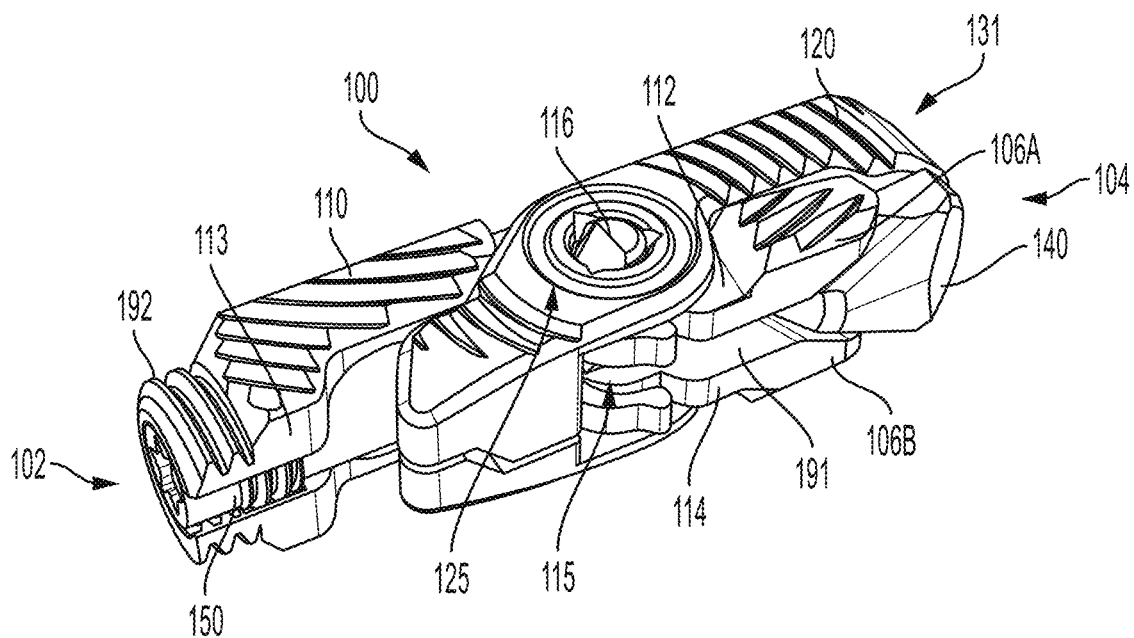
FIG. 1 is a perspective view of an expandable bi-dimensional intervertebral implant in accordance with an exemplary embodiment of the subject disclosure in a collapsed or primary position.

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout this disclosure, various aspects of the exemplary embodiments can be presented in a range format. It should be understood that the description in range format is merely for convenience and brevity and should not be construed as an inflexible limitation on the scope of the exemplary embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments may be combined in any suitable manner in one or more embodiments. One skilled in the relevant art will recognize, in light of the description herein, that the exemplary embodiments can be practiced without one or more of the specific features or advantages of a particular embodiment. In other instances, additional features and advantages may be recognized in certain embodiments that may not be present in all embodiments of the subject disclosure.

Figure 2:
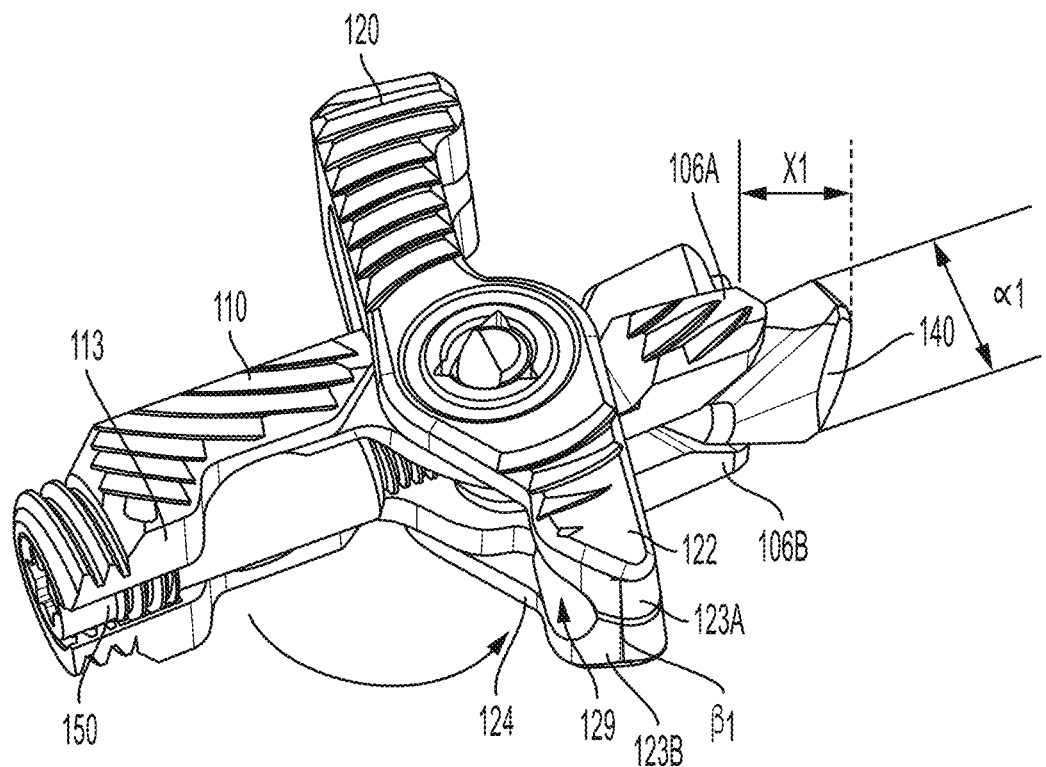
FIG. 2 is a perspective view of the expandable bi-dimensional intervertebral implant of FIG. 1 in a secondary position.
Figure 3:
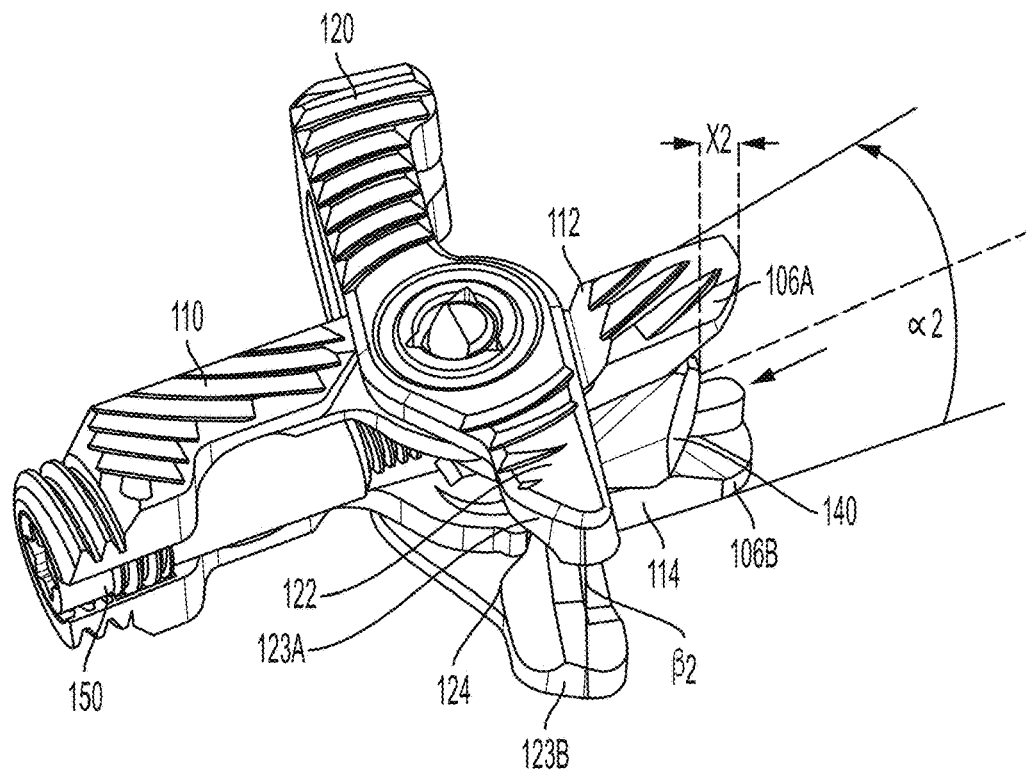
FIG. 3 is a perspective view of the expandable bi-dimensional intervertebral implant of FIG. 2 with the first and second bifurcated hinge arms in a second or expanded position.
Figure 4:
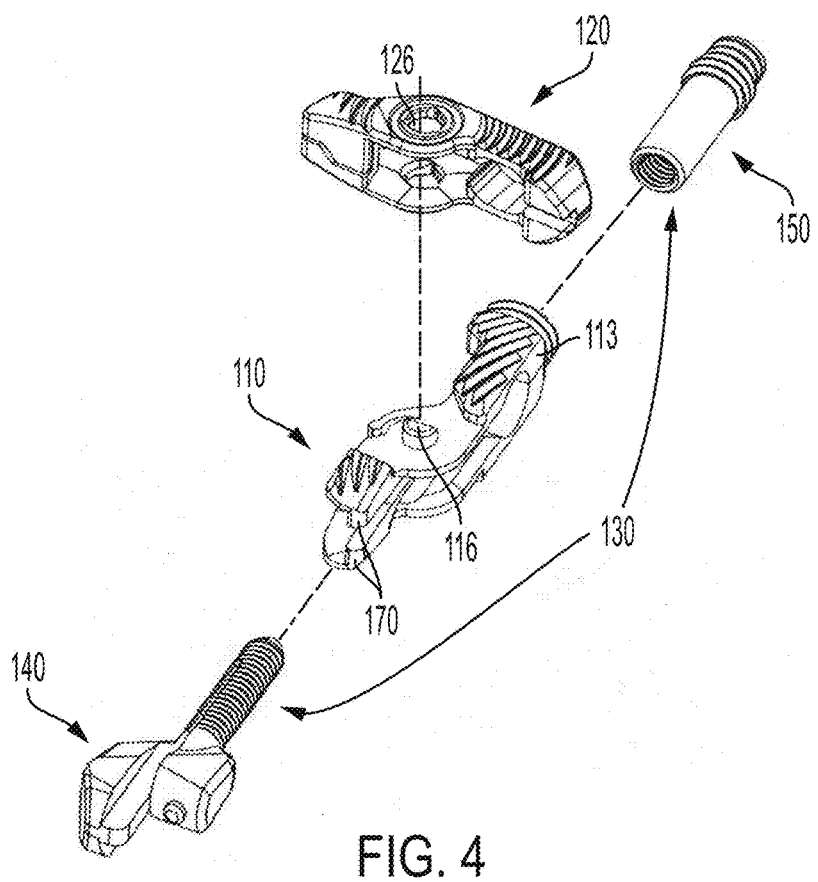
FIG. 4 is an exploded, perspective view of the expandable bi-dimensional intervertebral implant of FIG. 1.

Referring to FIGS. 1-4, there is shown an exemplary embodiment of an expandable bi-dimensional intervertebral implant 100 in accordance with the subject disclosure. As shown in FIG. 4, the intervertebral implant 100 includes a first hinge arm 110, a second hinge arm 120 pivotably connected to the first hinge arm, and a translation member 130 movable relative to the first hinge arm and the second hinge arm. In general, the translation member 130 biases the first hinge arm 110 and the second hinge arm 120. As further discussed below, the translation member 130 includes a translation element 140 and a shaft 150 operatively engaged with the translation element 140.

The expandable bi-dimensional intervertebral implant 100 can be manufactured from a number of materials including metals e.g., titanium, stainless steel, titanium alloys, non-titanium metallic alloys, polymers, e.g., high-density polyethylene, and polyetheretherketone (PEEK), and ceramics e.g., silicon nitride ($Si_3N_4$), zirconium oxide ($ZrO_2$), and silver oxide ($Ag_2O$), and other suitable materials, both radiopaque and radiolucent. The expandable bi-dimensional intervertebral implant 100 can be manufactured from more than one material. In some exemplary embodiments, the expandable bi-dimensional intervertebral implant 100 is made from a primary base material and a secondary element such that the implant 100 can be made from at least about 51% of the primary base material and from about 0% to about 49% of the secondary element. In other embodiments, an expandable bi-dimensional intervertebral implant 100 can be manufactured from multiple materials by integrating the secondary element within the primary base material and/or by coating a surface of the primary base material with the secondary element.

Advantageously, ceramics such as silicon nitride produce alkaline compounds that are lethal to bacteria and promote osteo-integration. See Pezzotti, G. et al. Silicon Nitride Bioceramics Induce Chemically Driven Lysis in *Porphyromonas gingivalis. Langmuir* 32, 3024-3035 (2016) and Webster, T J et al. "Anti-infective and osteointegration properties of silicon nitride, poly(ether ether ketone), and titanium implants." *Acta biomaterialia* vol. 8, 12 (2012): 4447-54. Additionally, silicon nitride has osteoinductive, osteoconductive, hydrophilic, and/or germicidal surface properties that promote bone formation and tissue development. Silicon nitride is also inherently resistant to bacteria and biofilm formation. See e.g., Ishikawa, Masahiro et al. "Surface topography of silicon nitride affects antimicrobial and osseointegrative properties of tibial implants in a murine model." *Journal of biomedical materials research.* Part A vol. 105, 12 (2017): 3413-3421. doi:10.1002/jbm.a.36189.

As oriented in FIGS. 1, 2, 3, 6A, 6B, 7, 8A and 8B, the second hinge arm 120 is movable between a primary position (FIGS. 1, 6A, 6B and 8A) and a secondary position (FIGS. 2, 3, 7 and 8B) relative to the first hinge arm 110.

Figure 9:
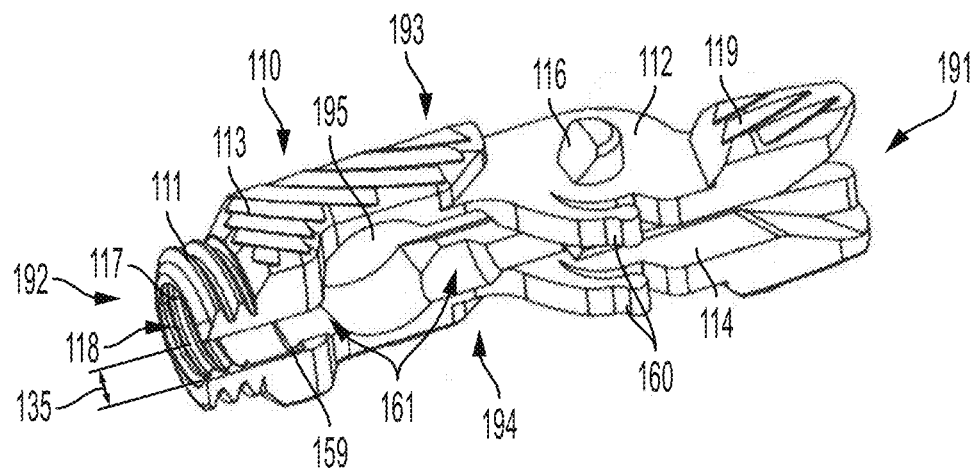
FIG. 9 is a side perspective view of a first hinge arm of the expandable bi-dimensional intervertebral implant of FIG. 1.

As shown in FIGS. 1-4 and 9, the first hinge arm 110 includes an anterior end 191 and a posterior end 192. The anterior end 191 of the first hinge arm 110 is configured as a first bifurcated hinge arm having a first arm segment 112 and a second arm segment 114. The first and second arm segments 112, 114 extend from a base 113 about the posterior end 192 of the first hinge arm 110. As shown in FIG. 9, the first hinge arm 110 includes a through hole 118 about its posterior end 192 for receiving the shaft 150 of the translation member 130 therethrough. The through hole 118 is a posterior facing through hole and is located about the posterior end 192 of the first hinge arm 110. The through hole 118 contains threads 117 along its inner surface for engaging corresponding threads on the translation member 130. A longitudinal axis of the through hole 118 extends in the same direction as a longitudinal axis or extent of the translation member 130. The posterior end 192 of the first hinge arm 110 further includes external threads 111 about its outer surface for engaging a drive instrument interface (not shown). The first hinge arm 110 further includes an upper surface 193, a lower surface 194 and a through hole 195 that passes between the upper surface 193 and the lower surface 194. The through hole has a central longitudinal axis transverse to the direction of the longitudinal axis of the first hinge arm 110.

The first hinge arm 110 also includes an inner cavity 161 between the upper surface 193 and lower surface 194 for mountably receiving and retaining the shaft 150 of the translation member 130. There is a flange 159 adjacent a posterior end of the cavity 161 which serves as a stop or limit for limiting movement of the shaft 150 therein.

The through hole 195, in an exemplary embodiment, is sized to receive bone graft or similar bone growth inducing material to be packed in a center of the implant 100. In other words, the through hole 195 can be configured to enable bone graft material deposited within the implant 100 to engage, contact and/or fuse with an adjacent vertebral body. The upper surface 193 may be referred to as an outer surface and/or a superior surface. Similarly, the lower surface 194 may be referred to as an inner surface and/or an inferior surface.

Figure 6A:
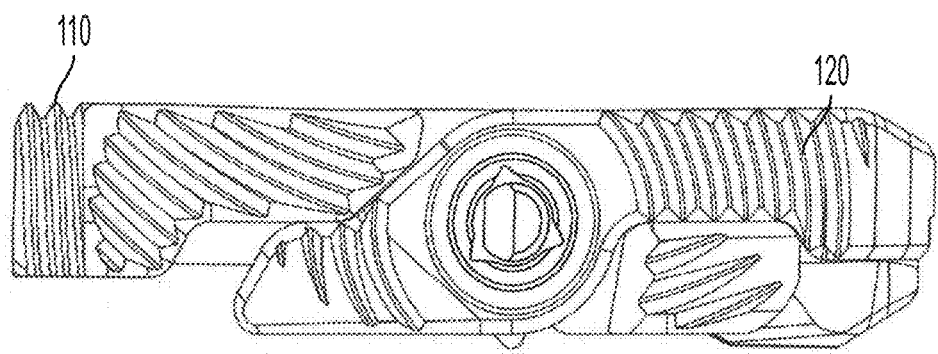
FIG. 6A is a top view of the expandable bi-dimensional intervertebral implant of FIG. 1 in the collapsed or primary position.
Figure 6B:
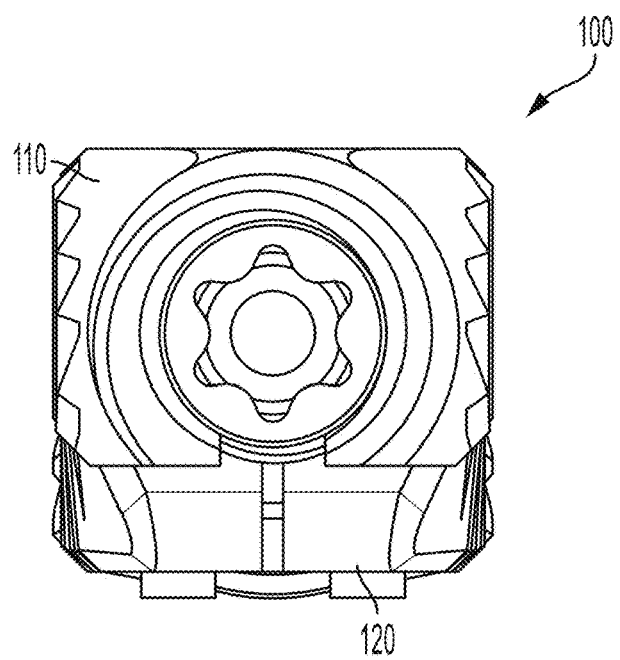
FIG. 6B is a rear view of the expandable bi-dimensional intervertebral implant of FIG. 1 in the collapsed or primary position.
Figure 7:
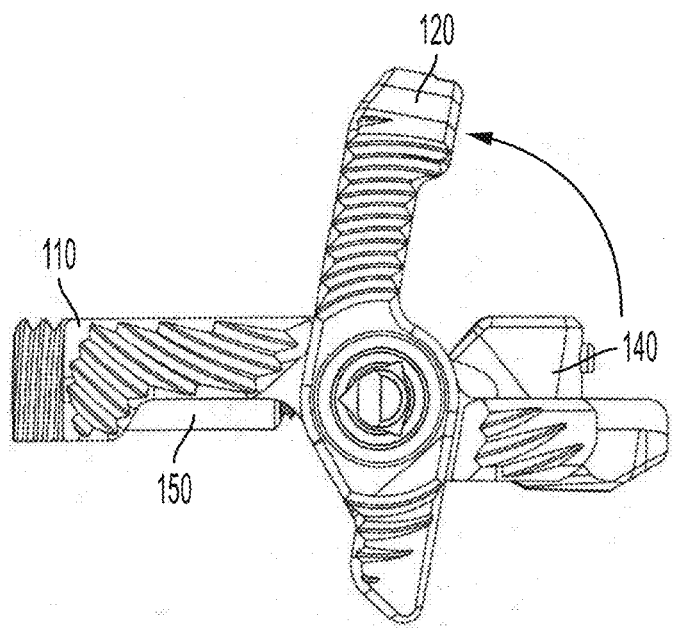
FIG. 7 is a top view of the expandable bi-dimensional intervertebral implant of FIG. 1 in the secondary position.
Figure 10:
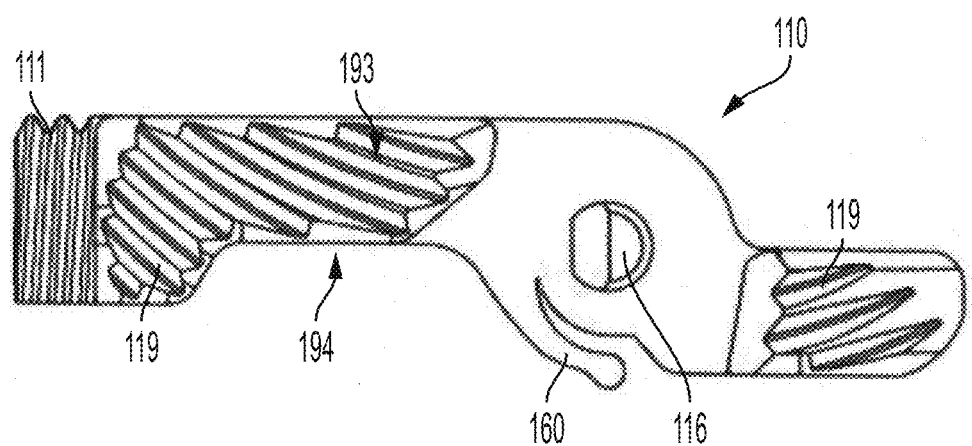
FIG. 10 is a top view of the first hinge arm of the expandable bi-dimensional intervertebral implant of FIG. 1.
Figure 22A:
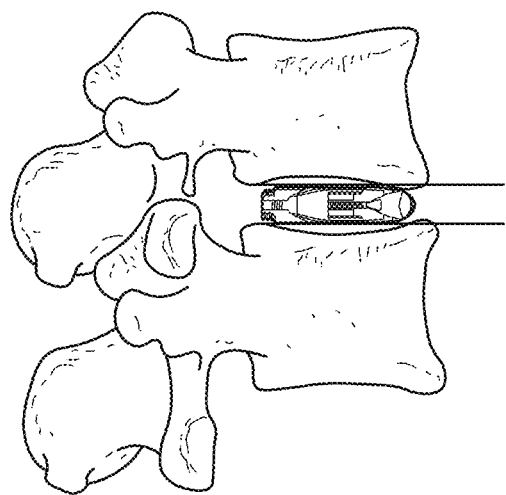
FIG. 22A is a side perspective view of the expandable bi-dimensional intervertebral implant of FIG. 1 illustrating the implant with a planar surface.
Figure 22B:
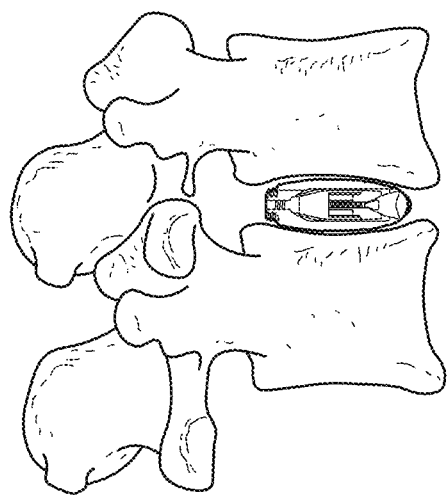
FIG. 22B is a side perspective view of the expandable bi-dimensional intervertebral implant of FIG. 1 illustrating the implant with a curved surface.

As shown in FIG. 10, the upper surface 193 of the first hinge arm 110 is generally planar to allow the upper surface 193 of the first hinge arm 110 to engage with adjacent vertebral bodies. However, as shown in FIG. 22B, the upper surface 193 and/or lateral surfaces of the first hinge arm can be curved convexly or concavely to allow for a greater or lesser degree of engagement with adjacent vertebral bodies. It is also contemplated that the upper surface 193 and/or lateral surfaces of the first hinge arm can be generally planar (FIG. 22A) but include a generally straight ramped surface or a curved ramp surface to allow for engagement with adjacent vertebral bodies in a lordotic fashion. In an exemplary aspect, the first hinge arm 110 is configured having a substantially trapezoidal-shaped posterior profile, as shown in FIG. 6B. However, the posterior profile of the first hinge arm 110 can be configured as any shape suitable for the foregoing intended use and/or design criteria, e.g., substantially rectangular, triangular and the like.

Figure 27:
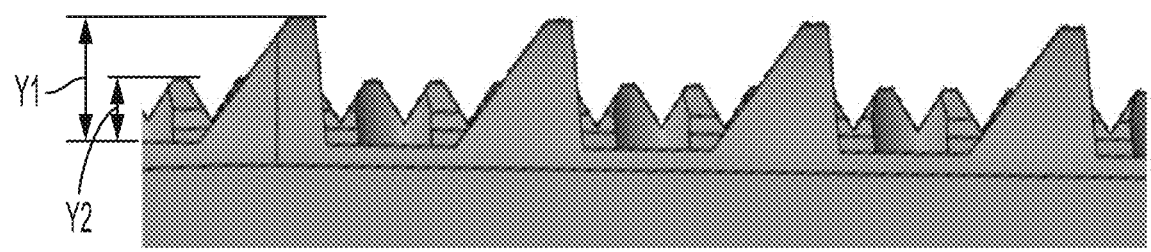
FIG. 27 is an isolated side view of a variable density external surface of the expandable bi-dimensional intervertebral implant of FIG. 1.
Figure 28:
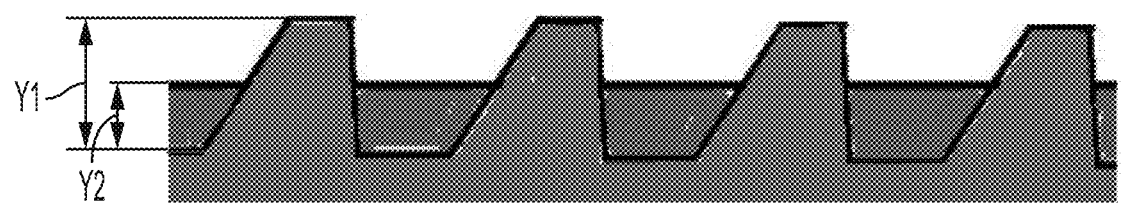
FIG. 28 is an isolated side view of a variable textured teethed zone of the expandable bi-dimensional intervertebral implant of FIG. 1.
Figure 29:
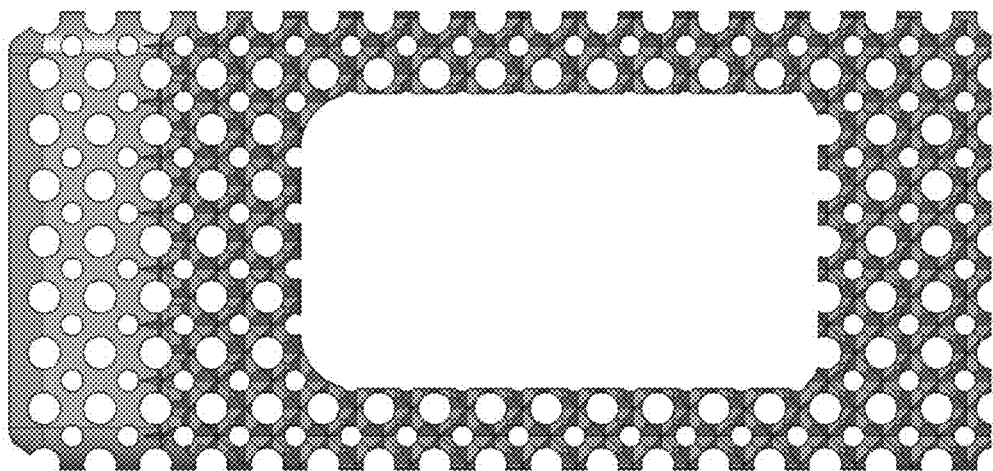
FIG. 29 is an isolated top view of a textured surface of the expandable bi-dimensional intervertebral implant of FIG. 1.
Figure 30A:
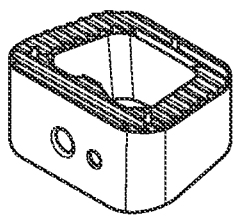
FIGS. 30A-E are perspective views of various footprints of interbody fusion devices applicable for use with the subject disclosure.
Figure 30B:
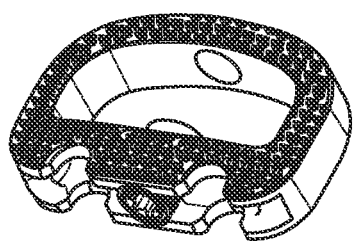
Figure 30C:
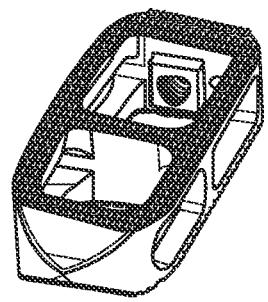
Figure 30D:
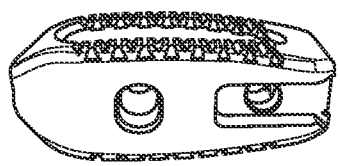
Figure 30E:
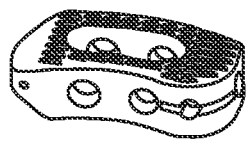

In an aspect of the exemplary embodiment, the first hinge arm 110 includes texturing 119 along its outer surfaces to aid in gripping adjacent vertebral bodies during implantation of the implant 100. As shown in FIG. 9, the texturing 119 can be positioned on outer surfaces of the first arm segment 112 and the second arm segment 114. As shown in FIGS. 27-29, it is to be understood that the texturing 119 can be a variable density external surface (FIG. 27) or a variable textured teethed zone (FIG. 28). The variable density external surface can be developed using a topology optimization method and/or algorithm to create a lightweight bi-dimensional intervertebral implant having a desired variable feel or firmness and/or shape retention in one region of the implant relative to another region of the implant. Such topology optimization can be utilized to customize implants based on the needs of a particular patient. The texturing can include, but is not limited to, teeth, ridges, friction increasing elements, patterned divots, through holes, keels or gripping or purchasing projections. As shown in FIGS. 27 and 28, the texturing can be a multi-density and/or variable textured teethed zone having a height Y1 with a trabecular zone having a height Y2.

The variable density external surface is achieved by controlling the volume to porosity ratio of the subject external surface. For example, the malleability/deformability of the surface can be achieved by decreasing the volumetric density (i.e., increasing porosity) and by decreasing the thickness of the external surface layer. This can be accomplished through various techniques including, but not limited to, additive manufacturing, subtractive manufacturing, chemical subtraction, laser texturing, and the like. Such methods are disclosed, for example, in U.S. Pat. Nos. 10,596,660 and 10,864,070, the disclosures of which are hereby incorporated by reference in their entirety for all purposes.

Figure 12:
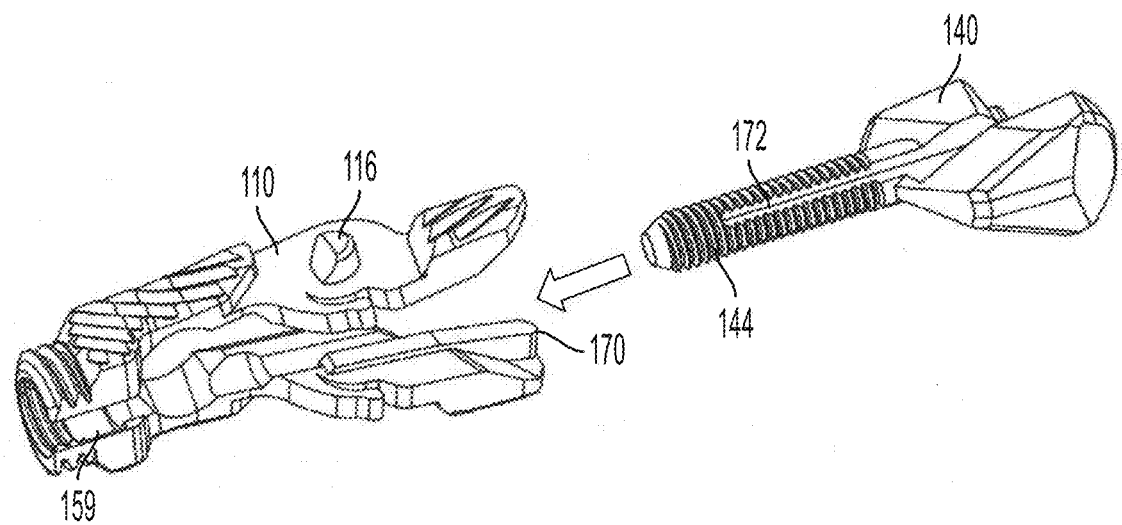
FIG. 12 is a side perspective view of a translation element for engaging the first hinge arm of the expandable bi-dimensional intervertebral implant of FIG. 1.

Referring now to FIGS. 4 and 12, the first hinge arm 110 further includes one or more mating elements, e.g., a pair of anterior male tracks 170. The anterior male track 170 operatively engages with complementary or corresponding mating elements on the translation member 130 to form a slidable joint. That is, the translation member 130 is configured to slideably engage the first hinge arm 110. The slideable joint advantageously enables the first hinge arm 110 to move from a first position to a second position. As further discussed below, the anterior male track 170 prevents dislocation of the translation member 130 when the implant 100 is assembled.

As shown in FIGS. 1-4, the first hinge arm 110 further includes a radial hinge, e.g., radial protrusion 116 on each of its upper and lower surfaces. Specifically, the radial protrusion 116 is located about a mid-portion 115 of the first hinge arm 110. As further discussed below, the radial protrusion 116 of the first hinge arm 110 operatively engages the second hinge arm 120 when the first hinge arm 110 engages the second hinge arm 120.

Figure 11:
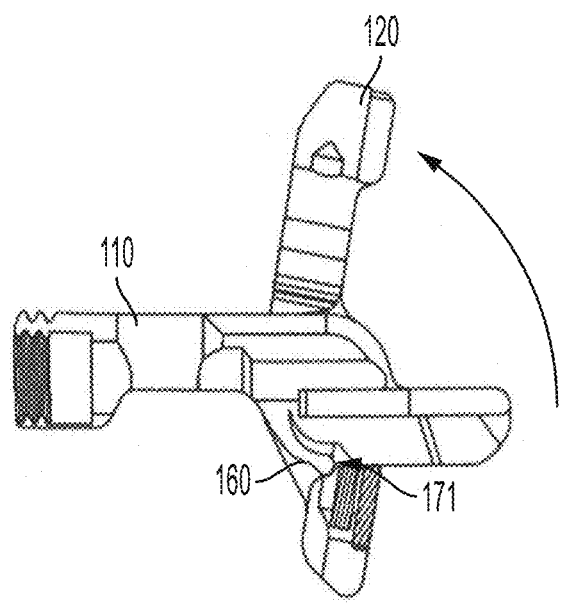
FIG. 11 is a top cross-sectional view of the expandable bi-dimensional intervertebral implant of FIG. 1.
Figure 18:
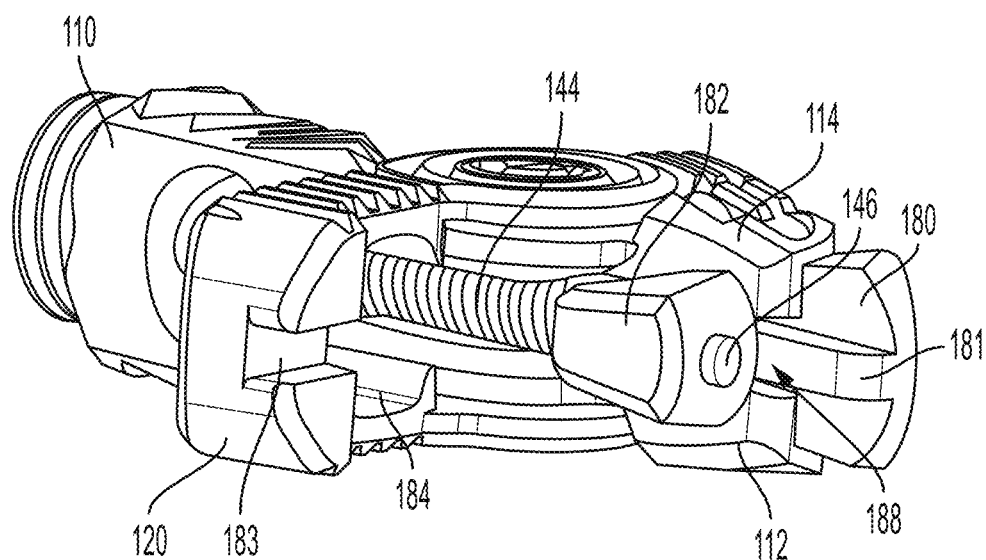
FIG. 18 is another side perspective view of the expandable bi-dimensional intervertebral implant of FIG. 1 in a secondary position.

Referring now to FIGS. 9 and 10, the first hinge arm 110 includes a locking tab 160 for securing the first hinge arm 110 and the second hinge arm 120 in a secondary position. While the discussion below refers to the locking tab 160 in the singular, it is to be understood that the first arm segment 112 and the second arm segment 114 each include respective locking tabs (FIG. 9). Specifically, as further discussed below, the locking tab 160 projects laterally away from the first hinge arm 110 and is received within a recess 171 of the second hinge arm 120 (FIG. 11). Additionally, when the implant 100 is assembled, there is a gap 188 (FIG. 18) formed between the first arm segment 112 and the second arm segment 114. The gap 188 slideably receives a cooperating track 181 on the translation element 140. The track 181 is configured as shown in FIG. 18, e.g., as a tongue. However, it can be configured as any other suitable element including, but not limited to, a ridge, tooth or projection.

Figure 13A:
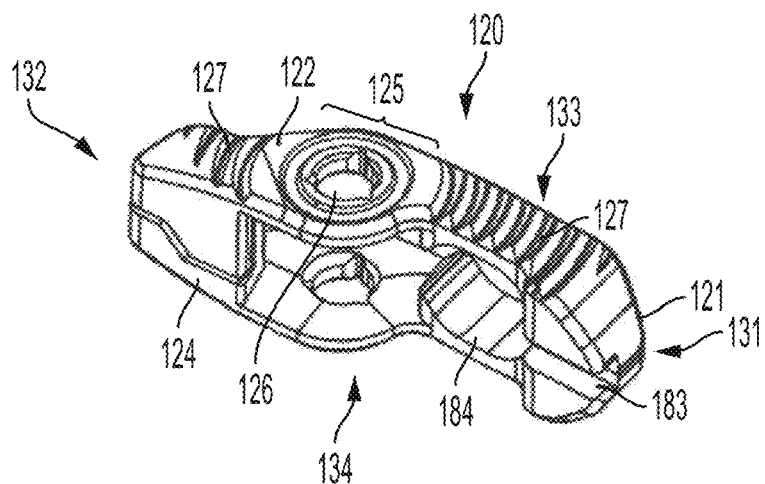
FIG. 13A is a side perspective view of a second hinge arm of the expandable bi-dimensional intervertebral implant of FIG. 1 in a first position.

As shown in FIGS. 1-4 and 13A, the second hinge arm 120 includes an anterior end 131 and a posterior end 132 and is pivotably connected to the first hinge arm 110. The second hinge arm 120 further includes an upper surface 133 and a lower surface 134. The posterior end 132 is configured as a second bifurcated hinge arm having a first arm segment 122 and a second arm segment 124. The first and second arm segments 122, 124 extend from a base 121 about the anterior end 131 of the second hinge arm 120. In accordance with an aspect, the base 121 about the anterior end 131 is of unitary construction. As shown in FIGS. 4 and 13A, the second hinge arm 120 includes a through hole 126 about its mid-portion 125 extending in a direction transverse to its longitudinal axis for receiving respective radial protrusions 116 of the first hinge arm 110.

Figure 8A:
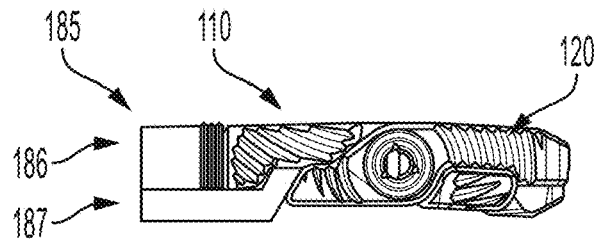
FIG. 8A is a top view of the expandable bi-dimensional intervertebral implant of FIG. 1 in the collapsed or primary position with an expansion instrument.
Figure 8B:
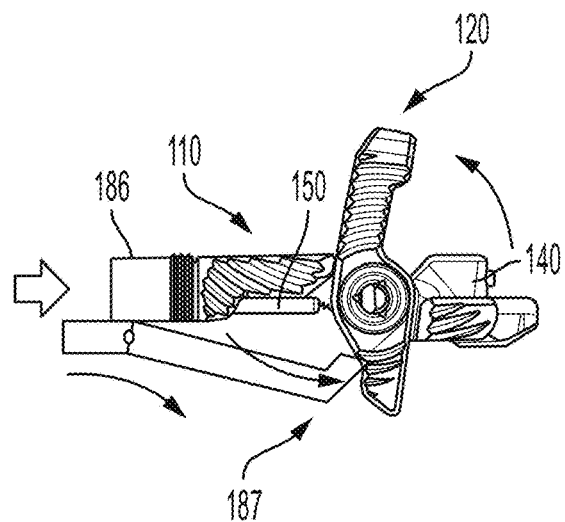
FIG. 8B is a top view of the expandable bi-dimensional intervertebral implant of FIG. 1 in the secondary position with an expansion instrument.

As shown in FIGS. 8A and 8B and further discussed below, a moving shaft 187 of a driving tool 185 is used to move the second hinge arm 120 from the primary position to the secondary position relative to the first hinge arm 110. Specifically, the second hinge arm 120 is rotated approximately ninety degrees such that its longitudinal axis is substantially perpendicular to a longitudinal axis of the first hinge arm 110 in the secondary position. The second hinge arm 120 is secured in the secondary position via the locking tab 160.

In an aspect of the exemplary embodiment, the second hinge arm 120 includes texturing 127 to aid in gripping adjacent vertebral bodies. The texturing 127 can be the same or similar texturing as described above for the first hinge arm 110. That is, similar to the texturing 119 of the first hinge arm 110, the texturing 127 can be a variable density external surface or a variable textured teethed zone.

Referring back to FIGS. 1-3 and 13A, the first arm segment 122 and second arm segment 124 form a rounded or concave recess 129 (FIG. 2) about the posterior end 132 of the second hinge arm 120 that is complementary shaped to the shaft 150 of the translation member 130 such that the shaft 150 is slidable along the second hinge arm 120 in the collapsed position. Additionally, as shown in FIGS. 13A, 17 and 18, the anterior end 131 of the second hinge arm 120 includes a recess 184 formed by its first and second arm segments 122, 124 for enclosing a lateral portion 182 (FIG. 16) of the translation element 140 in the collapsed position. The anterior end 131 of the second hinge arm 120 also includes a channel 183 complementary in shape to the cooperating track 181 on the translation element 140.

In accordance with an exemplary embodiment, at least one of the first hinge arm 110 and second hinge arm 120 comprises silicon nitride. Alternatively, both the first and second hinge arms can comprise silicon nitride, partially or fully. As previously discussed above, at least one of the first hinge arm 110 and second hinge arm 120 includes a variable density external surface and/or a variable textured teethed zone. That is, one or both the first and second hinge arms can comprise variable density external surfaces and/or variable textured teethed zones.

As shown in FIGS. 1-5 and 14-16, the translation member 130 includes a translation element 140 and a shaft 150 operatively engaged with the translation element 140 for moving the translation element 140 between an initial position and an engaged position. The translation member 130 can be formed from materials that contain osteoinductive, osteoconductive, and/or germicidal surface properties for promoting bone formation and tissue development, e.g., ceramics such as silicon nitride, zirconium oxide, silver oxide, and other suitable materials, and can also be formed from radiopaque or radiolucent materials such that the spacing between the first and second hinge arms can be visible on radiographs e.g., a polymer such as high-density polyethylene or polyetheretherketone (PEEK). In general, the translation member 130 is positioned between the first and second arm segments 112, 114 of the first hinge arm 110, and between the first and second arm segments 122, 124 of the second hinge arm 120.

The shaft 150 includes a head 152 and a body 155. The head 152 of the shaft 150 includes a mating feature or drive 156 for engaging the driving tool 185 (FIGS. 8A-B). The head 152 includes a threaded portion 154 having a larger diameter than a diameter of the body 155 so as to engage the flange 159 of the first hinge arm 110. The body 155 of the shaft 150 contains threads 158 along its inner surface for engaging the translation element 140.

Referring back to FIGS. 1-4 and 9, the shaft 150 is mounted within the first hinge arm 110 substantially flush with a posterior face of the first hinge arm. Specifically, the first hinge arm 110 includes the inner cavity 161 for mountably receiving the shaft 150 including the head 152 therein. Thus, when the shaft 150 is positioned within the cavity 161, the head 152 is substantially flush with the posterior face of the first hinge arm 110. When the implant is in a fully assembled configuration, the shaft 150 is attached to the first hinge arm 110 in a fixed axial position relative to the first hinge arm such that a rotational force applied by the driving tool 185 to the shaft results in translation of the translation element 140 between an initial position and an engaged position relative to the shaft and first hinge arm. That is, the translation element 140 translates toward the shaft 150 as the translation element moves from the initial position towards the engaged position.

Figure 15A:
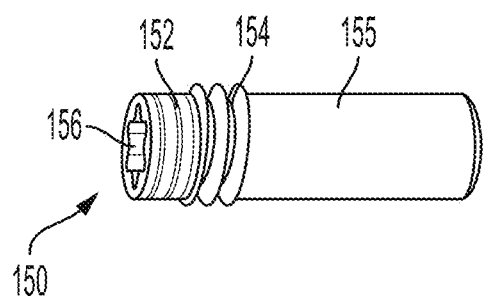
FIG. 15A is a side perspective view of a shaft of the translation member of the expandable bi-dimensional intervertebral implant of FIG. 1.
Figure 15B:
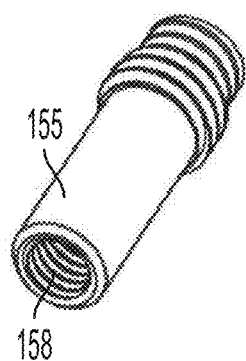
FIG. 15B is a perspective view of a shaft of the translation member of the expandable bi-dimensional intervertebral implant of FIG. 1.
Figure 16:
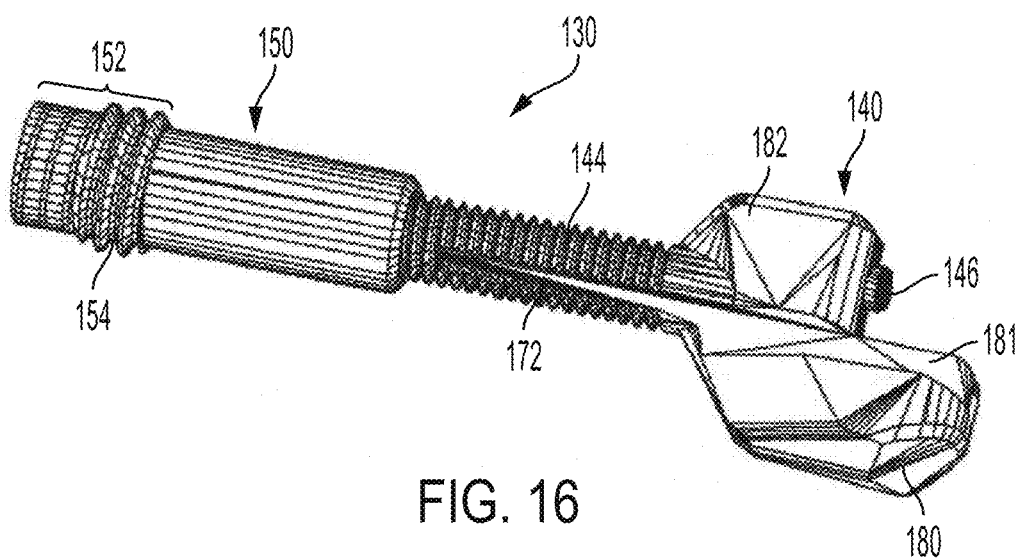
FIG. 16 is a perspective view of the translation member of the expandable bi-dimensional intervertebral implant of FIG. 1.
Figure 17:
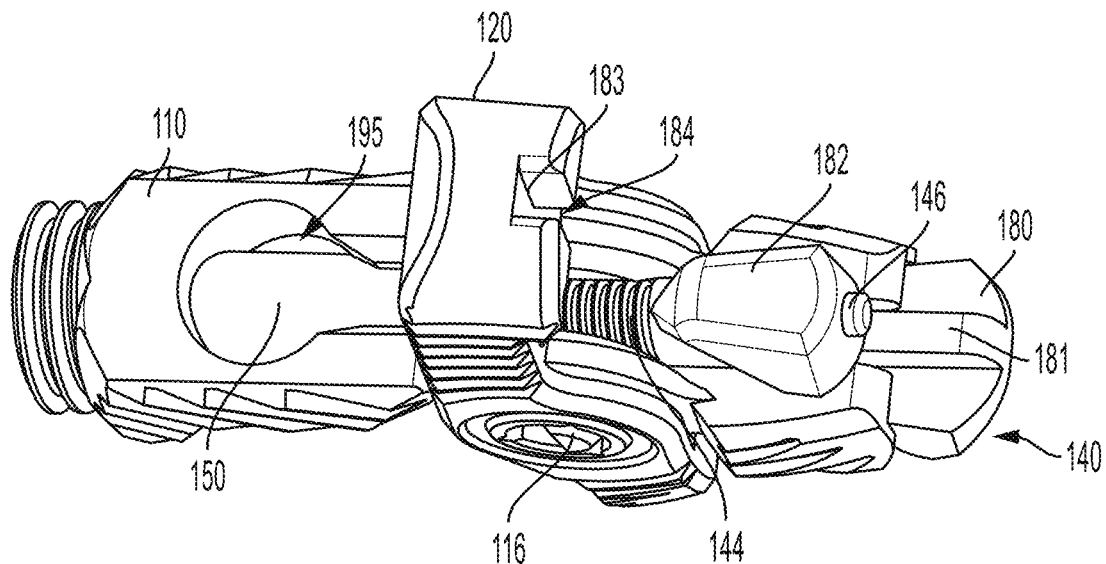
FIG. 17 is a side perspective view of the expandable bi-dimensional intervertebral implant of FIG. 1 in a secondary position.

The translation element 140 is configured as best shown in FIGS. 4, 5, 12, 14 and 16-18, and includes a threaded shaft 144 and a cam 180. A terminal end of the threaded shaft 144 is e.g., concave in shape, for example, a concave distal end or a distally facing concave end, but may alternatively be a convex or rounded end. As shown in FIGS. 15A, 15B, and 16, the threaded shaft 144 of the translation element 140 engages the inner threads 158 of the shaft 150. The translation element 140 also includes a cooperating retention track 172 along the threaded shaft 144 of the translation element 140 for operatively engaging corresponding male tracks 170 of the first hinge arm 110 to form a slidable joint. The slidable joint prevents dislocation of the translation member 130 as it engages the first hinge arm 110 during implantation of the implant 100 as well as rotation of the translation member upon rotation of the shaft. Preferably, the translation element includes a pair of cooperating retention tracks along opposite sides of the threaded shaft.

Figure 5:
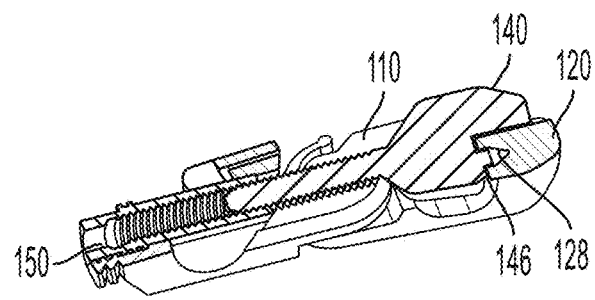
FIG. 5 is a side cross-sectional perspective view of the expandable bi-dimensional intervertebral implant of FIG. 1 in the collapsed or primary position.

As shown in FIG. 5, the anterior end of the translation element 140 includes a detent 146 for operatively engaging the second hinge arm 120 at a predetermined location when in the primary position. That is, the detent 146 extends proud of the anteriorly facing end and is sized and shaped to be received within a recess 128 of the second hinge arm 120. The detent 146 can also alternatively be formed of various other configurations that allow it to properly engage the recess 128 of the second hinge arm 120, such as being nipple shaped, dome shaped, or any other detent configuration suitable for the foregoing intended use. The detent 146 is pressed into the recess 128 and secures the second hinge arm 120 in the primary position to prevent expansion of the implant 100 during implantation into the patient. In sum, the detent 146 prevents the second hinge arm 120 from breaking out prematurely during implantation.

Figure 19:
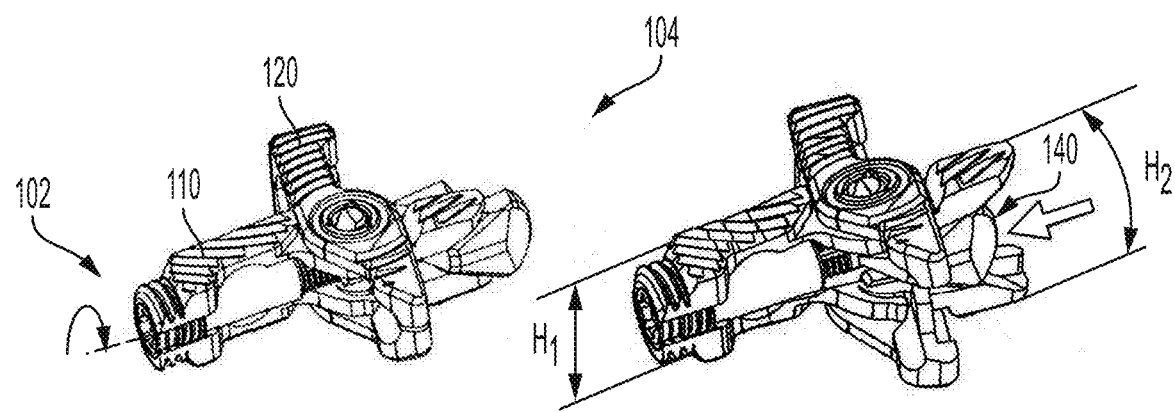
FIG. 19 is a side perspective view of the expandable bi-dimensional intervertebral implant of FIG. 1 in a secondary position and with the first and second bifurcated hinge arms in a second or expanded position.

As shown in FIGS. 14 and 16-21, the cam 180 includes a camming head 180 that is configured as a substantially trapezoidal shaped cam having an upper camming surface and a lower camming surface. The cam 180 further includes the T-shaped track 181 along its medial side that is complementary shaped to the gap 188 formed between the first arm segment 112 and the second arm segment 114 of the first hinge arm 110. The gap 188 slideably receives the T-shaped track 181 when the translation member moves toward the engaged position. As the translation member 130 is translated towards the engaged position, the camming head biases the first arm segment 112 and the second arm segment 114 of first hinge arm 110 outwardly or away from each other to move the first hinge arm 110 from the first position to the second position, i.e., an expanded position. Similarly, the biasing force from the camming head causes the first arm segment 112 and the second arm segment 114 of the first hinge arm 110 to bias the respective first arm segment 122 and second arm segment 124 of the second hinge arm 120 outwardly or away from each other to move the second hinge arm from the first position to second position, i.e., an expanded position (FIG. 19).

In sum, the cam 180 of the translation element 140 engages the first and second hinge arms 110, 120. That is, as the cam 180 translates toward the shaft 150, the cam biases the first hinge arm 110 to move from a first position to a second position and biases the second hinge arm 120 to move between a first position and a second position. In other words, the cam 180 of the translation member 130 splays the first and second hinge arms 110, 120. The expandable bi-dimensional intervertebral implant 100 can advantageously transition between a fully collapsed position (FIG. 1), a secondary position (FIG. 2), and an engaged or expanded position (FIG. 3).

Figure 13B:
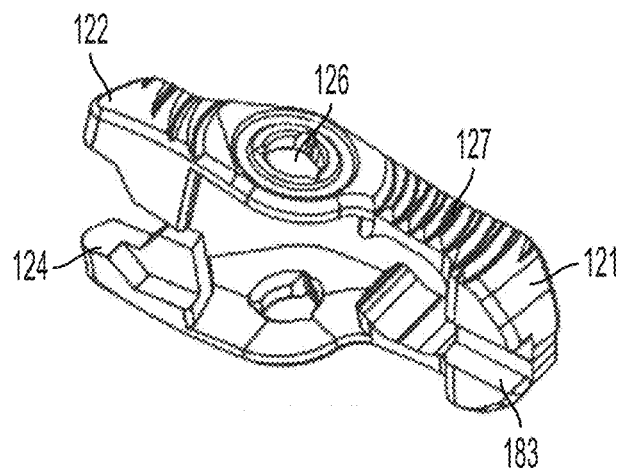
FIG. 13B is a side perspective view of a second hinge arm of the expandable bi-dimensional intervertebral implant of FIG. 1 in a second or expanded position.
Figure 14:
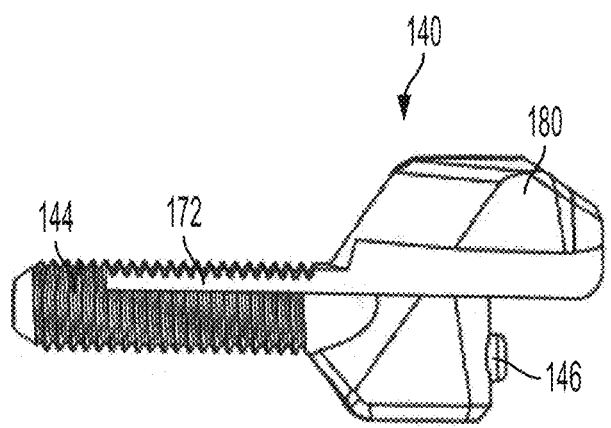
FIG. 14 is a bottom view of a translation element of the translation member of the expandable bi-dimensional intervertebral implant of FIG. 1.

In an aspect of the exemplary embodiment, the first hinge arm 110 includes free ends 106A-B movable between the first position and the second position. In the first position (FIG. 2), the free ends 106A-B of the first hinge arm segments 112, 114 are spaced apart a first distance $\alpha 1$. In the second position (FIG. 3), the free ends 106A-B are spaced apart a second distance $\alpha 2$ greater than the first distance $\alpha 1$. Similar to the first hinge arm 110, the second hinge arm 120 includes free ends 123A-B movable between the first position and the second position, when in the secondary position. In the first position (FIG. 2), the free ends 123A-B of the second hinge arm segments 122, 124 are spaced apart a first distance 131. In the second position (FIG. 3), the free ends 123A-B are spaced apart a second distance $\beta 2$ greater than the first distance $\beta 1$. As shown in FIG. 19, in the engaged position, a posterior end 102 of the expandable bi-dimensional intervertebral implant 100 has a first height H1 and an anterior end 104 of the implant has a second height H2 greater than the first height H1. The second height H2 can vary e.g., it can range from about 0 mm to 10 mm. The height varies depending upon the amount of splaying as the translation member 130 moves along the corresponding male tracks 170 to splay the respective segments of first and second hinge arms 110, 120. In other words, the expandable bi-dimensional intervertebral implant provides for variable adjustment of the amount of asymmetrical expansion. In accordance with an aspect shown in FIGS. 3 and 13B, the first and second arm segments 122, 124 of the second hinge arm 120 are tapered to allow for splaying without interference.

With reference to FIGS. 1-4 and 9, the expandable bi-dimensional intervertebral implant 100 is assembled in a modular fashion. The first hinge arm 110 and second hinge arm 120 are pivotably or hingedly connected. Specifically, the pair of radial protrusions 116 on each of the upper and lower surfaces around mid-portion 115 of the first hinge arm 110 operatively engage respective through holes 126 on each of the upper and lower arm segments around mid-portion 125 of the second hinge arm 120. Thereafter, the shaft 150 of the translation member 130 is mounted within the cavity 161 of the first hinge arm 110. As shown in FIGS. 12 and 14-16, the threaded shaft 144 of the translation element 140 engages the inner threads 158 of the shaft 150. As the translation element 140 engages the inner threads 158, the anterior male tracks 170 of the first hinge arm 110 slideably engage the cooperating retention tracks 172 on the threaded shaft 144 of the translation element 140 to form a slidable joint.

Referring now to FIGS. 8A and 8B, the driving tool 185 having a fixed shaft 186 and moving shaft 187 is used to expand the implant 100 when implanted in the body. The fixed shaft 186 is rotatably connected to the mating feature 156 on the head 152 of the shaft 150. A force applied on the moving shaft 187 causes the moving shaft to bias the second hinge arm 120 from the primary position (FIG. 8A) to the secondary position (FIG. 8B). In doing so, the second hinge arm 120 is rotated approximately ninety degrees such that its longitudinal axis is substantially perpendicular to a longitudinal axis of the first hinge arm 110. As shown in FIG. 11, the second hinge arm 120 is secured in position by the locking tab 160 of the first hinge arm 110. That is, the locking tab 160 is received within the recess 171 of the second hinge arm 120 to prevent the second hinge arm from rotating back to the primary position or away from the secondary position.

Referring now to FIGS. 3, 8A-8B, 11, 15A, 15B, 16 and 19, a rotational force applied on the head 152 of the shaft 150 for example via a torque tool applied to the mating feature 156, causes the threaded shaft 144 of the translation element 140 to engage the inner threads 158 of the shaft. As the translation element 140 engages the inner threads 158, the anterior male tracks 170 of the first hinge arm 110 slideably engage the cooperating retention tracks 172 on the threaded shaft 144 of the translation element 140. As a result, the translation element 140 translates toward the shaft 150 as the translation member moves from the initial position towards the engaged position.

As the translation member 130 is translated towards the engaged position, the cam 180 biases the first arm segment 112 and the second arm segment 114 of first hinge arm 110 outwardly to move the first hinge arm 110 from the first position to the second position. As a result, the first and second arm segments 112, 114 bias the first and second arm segments 122, 124 of the second hinge arm outwardly to move the second hinge arm from the first position to the second position.

Referring now to FIGS. 2-4, in the first position (FIG. 2), an anterior end of the translation member 130 is anteriorly spaced a distance X1 from the anterior end 191 of the first hinge arm 110. In the second position (FIG. 3), the anterior end of the translation member 130 is posteriorly spaced a distance X2 from the anterior end 191 of the first hinge arm 110. As the translation member moves posteriorly, the space between the free ends 106A-B of the first hinge arm 110 increases ($\alpha 1 \rightarrow \alpha 2$). Similarly, the space between the free ends 123A-B of the second hinge arm 120 increases ($\beta 1 \rightarrow \beta 2$).

In some exemplary embodiments, the second distance $\alpha 2$ can be from about 25% to 100% greater than the first distance $\alpha 1$, including 20, 30, 40, 50, 60, 70, 80 and 90%. In other exemplary embodiments, the second distance $\alpha 2$ can be from about 50% to 100% greater than the first distance $\alpha 1$. In other embodiments, the second distance $\alpha 2$ can be from at least about 50% greater than the first distance $\alpha 1$. For example, the second distance $\alpha 2$ can be about 4 mm to 6 mm including 4.5, 5, and 5.5 mm greater than the first distance $\alpha 1$, but also less than 4 mm and greater than 6 mm. Similarly, in some exemplary embodiments, the second distance $\beta 2$ can be from about 25% to 100% greater than the first distance $\beta 1$, including 20, 30, 40, 50, 60, 70, 80 and 90%. In other exemplary embodiments, the second distance $\beta 2$ can be from about 50% to 100% greater than the first distance $\beta 1$. In other embodiments, the second distance $\beta 2$ can be from at least about 50% greater than the first distance $\beta 1$. For example, the second distance $\beta 2$ can be about 4 mm to 6 mm including 4.5, 5, and 5.5 mm greater than the first distance $\beta 1$, but also less than 4 mm and greater than 6 mm. Generally, the change in distance is caused by movement of the translation member from the initial position towards the engaged position. Those skilled in the art may appreciate that, in use, the distance between the free ends 106A-B of the first hinge arm and the distance between the free ends 123A-B of the second hinge arm can be respectively adjusted to accommodate an individual patient's needs.

Figure 20:
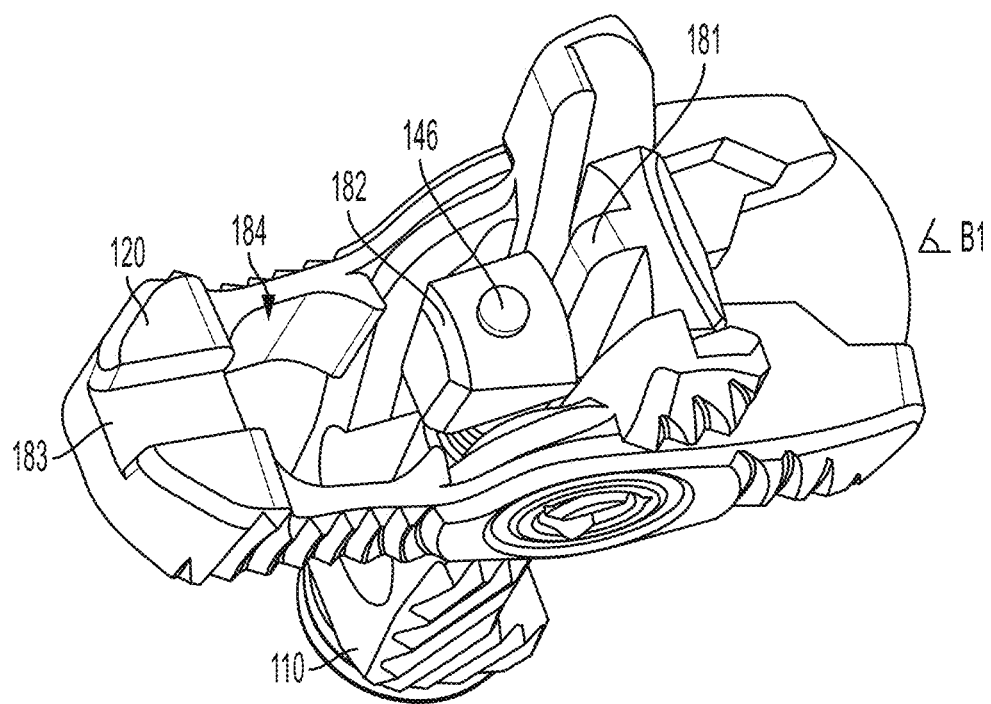
FIG. 20 is a front perspective view of the expandable bi-dimensional intervertebral implant of FIG. 1 with the first and second bifurcated hinge arms in a second or expanded position.
Figure 21:
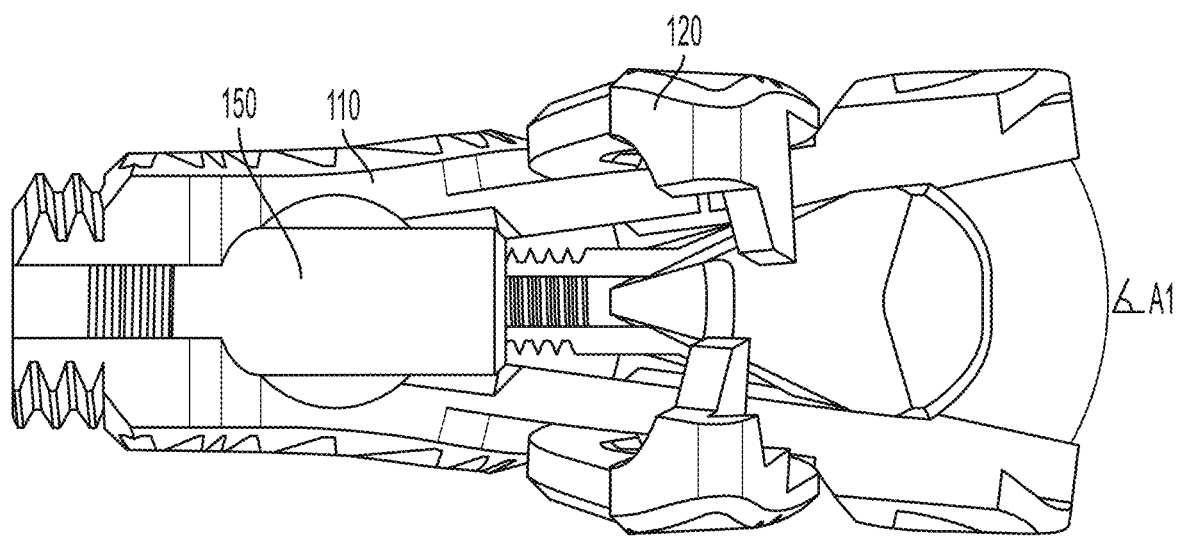
FIG. 21 is a side perspective view of the expandable bi-dimensional intervertebral implant of FIG. 1 with the first and second bifurcated hinge arms in a second or expanded position.
Figure 23A:
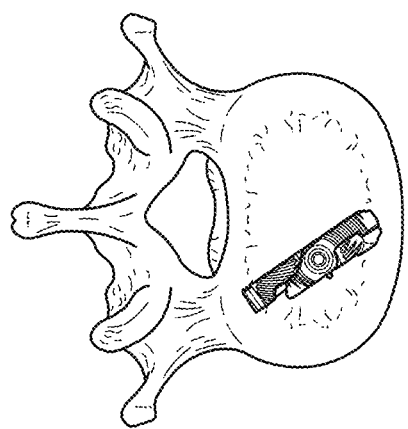
FIG. 23A is a top view of the expandable bi-dimensional intervertebral implant of FIG. 1 in the collapsed or primary position.
Figure 23B:
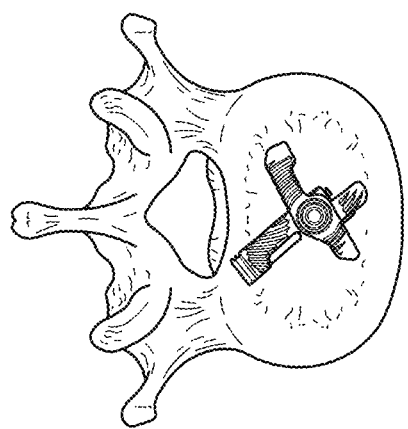
FIG. 23B is a top view of the expandable bi-dimensional intervertebral implant of FIG. 1 in the secondary position.
Figure 24A:
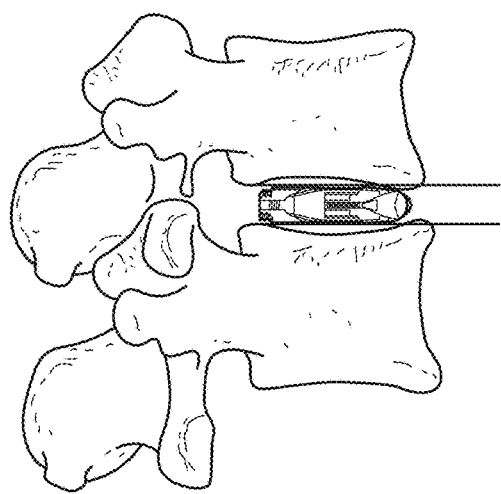
FIG. 24A is a side perspective view of the expandable bi-dimensional intervertebral implant of FIG. 1 in the collapsed or primary position.
Figure 24B:
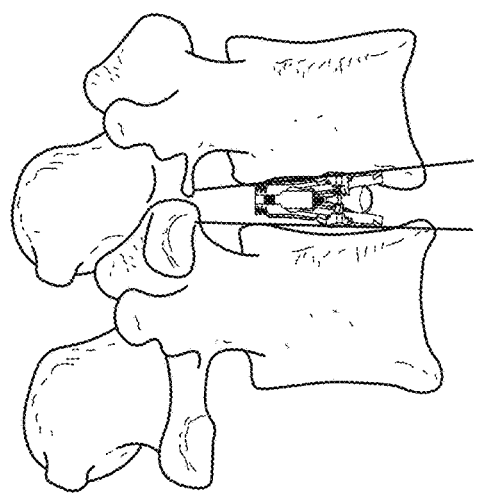
FIG. 24B is a side perspective view of the expandable bi-dimensional intervertebral implant of FIG. 1 with the first and second bifurcated hinge arms in a second or expanded position.

In the second position, the implant 100 achieves a lordotic angular expansion. As shown in FIGS. 3, 20 and 21, in the second position (i.e., expanded position), the free ends 106A-B of the first hinge arm 110 are spaced apart distance α2 and create an angle A1 (FIG. 21) between a longitudinally extending axis of the first arm segment 112 and a longitudinally extending axis of the second arm segment 114. In some exemplary embodiments, the angle A1 can be from about 0 to 30 degrees. Similarly, the free ends 123A-B of the second hinge arm 120 are spaced apart distance β2 and create an angle B1 (FIG. 20) between a longitudinally extending axis of the first arm segment 122 and a longitudinally extending axis of the second arm segment 124. Similarly, in some exemplary embodiments, the angle B1 can be from about 0 to 30 degrees. As such, the overall implant achieves an asymmetric overall expansion or in other words a substantially trapezoidal profile capable of lordotic angular expansion of the spine. After implantation in the body of a patient, the implant can transition between a fully collapsed position (FIGS. 23A and 24A) to an engaged position with lordotic angular expansion (FIGS. 23B and 24B).

While the subject disclosure discusses an exemplary embodiment of an expandable bi-dimensional intervertebral implant, the expandable bi-dimensional intervertebral implants discussed herein can be used with or in combination with various other interbody fusion devices such as those shown in FIGS. 30A-30E having various footprints including, but not limited to, transforaminal lumbar interbody fusion (TLIF), direct lateral interbody fusion (DLIF), and oblique lumbar interbody fusion (OLIF). Moreover, the expandable bi-dimensional intervertebral implant described herein can be used with a secondary cage that can be a TLIF, DLIF, or OLIF device. Such cages are disclosed e.g., in U.S. Pat. Nos. 10,543,101 and 10,219,912, the disclosures of which are hereby incorporated by reference in their entirety for all purposes.

Figure 25A:
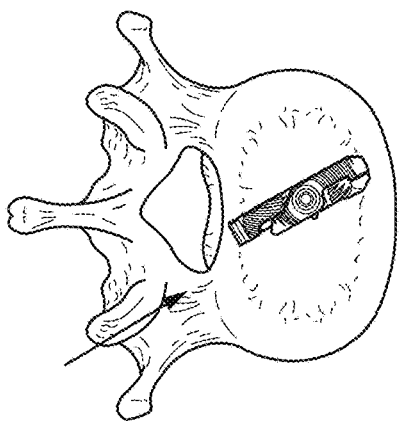
FIGS. 25A-D are top perspective views of various insertion trajectories applicable for use during implantation of the expandable bi-dimensional intervertebral implant of the subject disclosure.
Figure 25B:
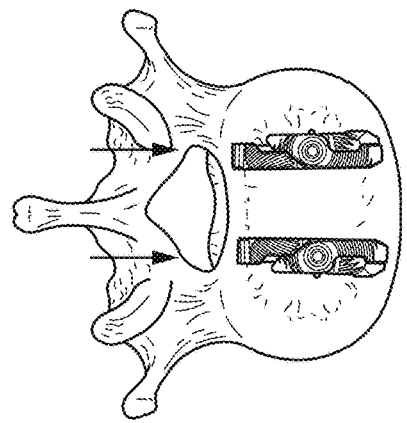
Figure 25C:
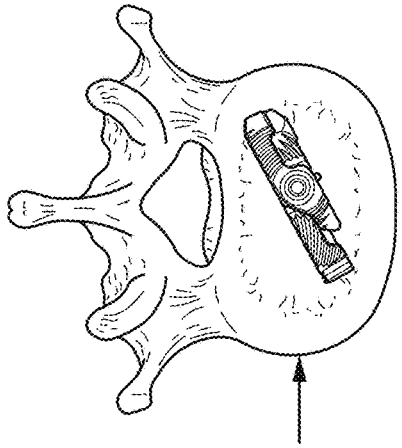
Figure 25D:
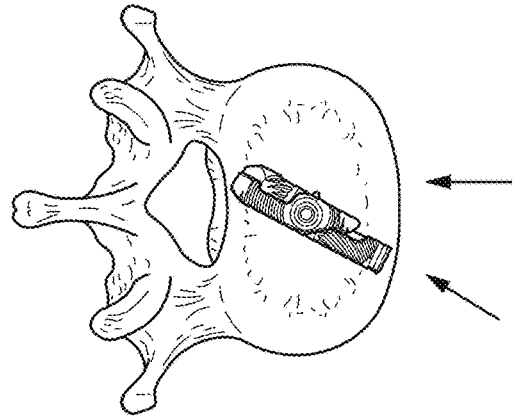
Figure 26A:
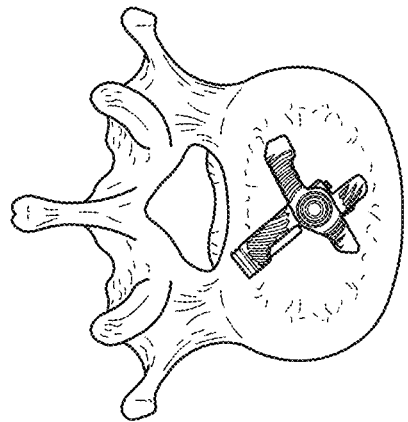
FIGS. 26A-D are top perspective views of the expandable bi-dimensional intervertebral implants illustrated in FIGS. 25A-D with the first and second bifurcated hinge arms in a second or expanded position.
Figure 26B:
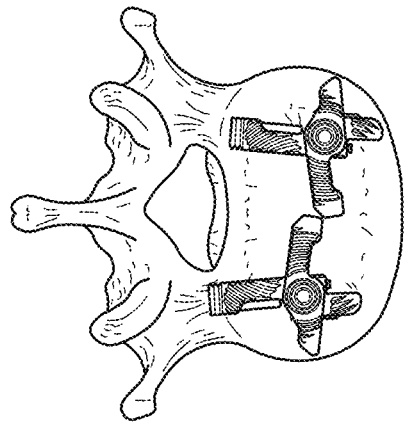
Figure 26C:
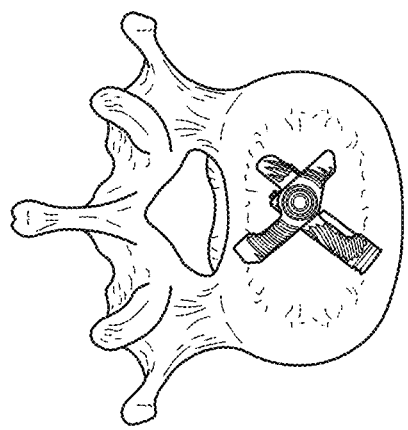
Figure 26D:
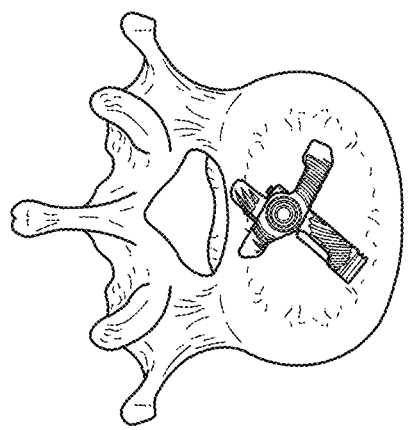

Referring now to FIGS. 25A-25D, the expandable bi-dimensional intervertebral implant 100 discussed herein can be implanted into the body of a patient at several different trajectories based on an individual patient's needs. During implantation, the implant 100 is in the collapsed position. Referring now to FIGS. 26A-26D, after implantation into the body, the implant 100 can be moved from the collapsed position to the engaged position. As shown in FIGS. 25B and 26B, the expandable bi-dimensional intervertebral implant described herein can be used with a secondary expandable bi-dimensional intervertebral implant.

The subject disclosure also provides a method of manufacturing an expandable bi-dimensional intervertebral implant. The method includes creating a computer aided design (CAD) model of a fully assembled implant. The method further includes the step of additively manufacturing the implant based on the CAD implant model with successive layers of material substantially parallel to a superior face of the first hinge arm. Advantageously, the layers being substantially parallel provides increased yield strength to the implant when normal loads are applied.

In contrast, if the additive layers extend in a direction in line with forces normal to a longitudinal length of the implant, the expandable bi-dimensional intervertebral implant will sheer more easily and have lower yield and compressive strength. However, if the additively manufactured layers extend at an angle relative to a longitudinal length of the implant, the line of forces acting on the implant will be transverse to the additive layers, thereby reducing the likelihood of sheering of the implant by increasing the parts' yield and compressive strength.

Figure 31:
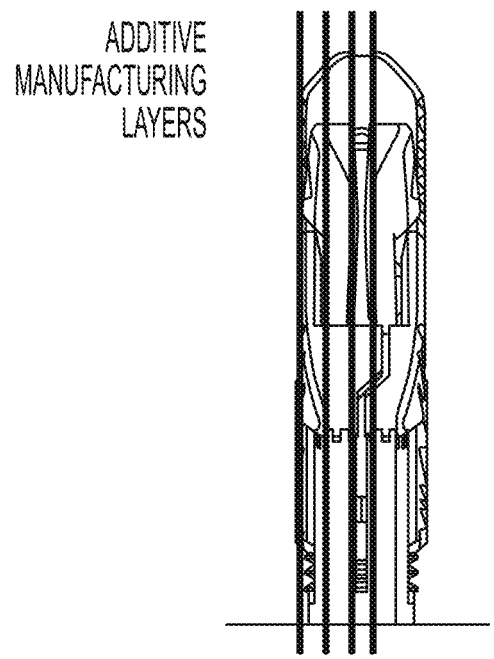
FIG. 31 is a perspective view of the expandable bi-dimensional intervertebral implant of FIG. 1 with lines depicting the layers formed by additive manufacturing of the implant.

Additionally, additive manufacturing advantageously allows the expandable bi-dimensional intervertebral implant to be formed as a single integral piece and constructed layer-by-layer, bottom-to-top, such that the components are integrally connected. In additive manufacturing, various types of materials in powder, liquid or granular form are deposited in layers. For additive manufacturing, a sloped surface on the radial protrusion 116 is required due to layer stacking and the orientation of the implant during 3D printing. That is, a sloped surface on the radial protrusion 116 avoids undesirable issues associated with the presence of overhangs in 3D printing such as curling, sagging, delamination, or collapsing. Utilizing a slope ensures that each new layer has enough support to remain intact and make 3D printing possible. As shown in FIG. 31, the deposited layers can be cured layer by layer until the entire component is complete. For example, an energized beam can be scanned over a bath of material to solidify a precise pattern of the material to form each layer until the entire component is complete. Similar techniques include, but are not limited to, rapid manufacturing, layered manufacturing, rapid prototyping, laser sintering, and electron beam melting. Such methods of additive manufacturing are generally disclosed in U.S. Pat. Nos. 9,783,718 and 10,596,660, the disclosures of which are hereby incorporated by reference in their entirety for all purposes.

It will be appreciated by those skilled in the art that changes could be made to the exemplary embodiments described above without departing from the broad inventive concept thereof. It is to be understood, therefore, that the subject disclosure is not limited to the particular exemplary embodiments disclosed, but it is intended to cover modifications within the spirit and scope of the subject disclosure as defined by the appended claims.

We claim:

1. An expandable bi-dimensional intervertebral implant comprising:
 a first hinge arm;
 a second hinge arm hingedly connected to a mid-portion of the first hinge arm about its mid-portion, and wherein the second hinge arm is movable between a primary position and a secondary position relative to the first hinge arm; and
 a translation member movable relative to the first hinge arm and the second hinge arm between an initial position and an engaged position, wherein in the engaged position, the translation member biases the first hinge arm to move from a first position to a second position and biases the second hinge arm to move between a first position and a second position.

2. The expandable bi-dimensional intervertebral implant of claim 1, wherein the first hinge arm is a first bifurcated hinge arm comprising a first arm segment and a second arm segment.

3. The expandable bi-dimensional intervertebral implant of claim 2, wherein in the first bifurcated hinge arm includes free ends movable between the first position and the second position.

4. The expandable bi-dimensional intervertebral implant of claim 3, wherein in the first position, the free ends of the first bifurcated hinge arms are spaced apart a first distance and in the second position, the free ends of the first bifurcated hinge arms are spaced apart a second distance greater than the first distance.

5. The expandable bi-dimensional intervertebral implant of claim 2, wherein the translation member is positioned between the first and second arm segments of the first hinge arm.

6. The expandable bi-dimensional intervertebral implant of claim 1, wherein the first hinge arm includes a locking tab for locking the first hinge arm and the second hinge arm in the secondary position.

7. The expandable bi-dimensional intervertebral implant of claim 1, wherein the first hinge arm includes a track engaging the translation member.

8. The expandable bi-dimensional intervertebral implant of claim 1, wherein the second hinge arm is a second bifurcated hinge arm comprising a first arm segment and a second arm segment.

9. The expandable bi-dimensional intervertebral implant of claim 8, wherein the second bifurcated hinge arm includes free ends movable between the first position and the second position.

10. The expandable bi-dimensional intervertebral implant of claim 9, wherein in the first position, the free ends of the second bifurcated hinge arms are spaced apart a first distance and in the second position, the free ends of the first bifurcated hinge arms are spaced apart a second distance greater than the first distance.

11. The expandable bi-dimensional intervertebral implant of claim 8, wherein the translation member is positioned between the first and second arm segments of the second hinge arm.

12. The expandable bi-dimensional intervertebral implant of claim 1, wherein the translation member comprises:
a translation element; and
a shaft operatively engaged with the translation element for moving the translation element between an initial position and an engaged position.

13. The expandable bi-dimensional intervertebral implant of claim 12, wherein the shaft is attached to the first hinge arm in a fixed axial position.

14. The expandable bi-dimensional intervertebral implant of claim 12, wherein the translation element comprises a cam for engaging the first and second hinge arms.

15. A method of manufacturing an expandable bi-dimensional intervertebral implant comprising:
additively manufacturing the expandable bi-dimensional intervertebral implant of claim 1 as a fully assembled component.

16. The method of claim 15, wherein each component of the expandable bi-dimensional intervertebral implant are additively manufactured with successive layers of material substantially parallel to a superior face of the first hinge arm.

17. An expandable bi-dimensional intervertebral implant comprising:
a first bifurcated hinge arm having a first arm segment and a second arm segment moveable relative to the first arm segment;
a second bifurcated hinge arm hingedly connected to the second bifurcated hinge arm having a first arm segment and a second arm segment moveable relative to the first arm segment, wherein the first bifurcated hinge arm and the second bifurcated hinge arm are movable between a primary position and a secondary position; and
a translation member between the first and second arm segments of the first and second bifurcated hinge arms and movable relative to the first bifurcated hinge arm and the second bifurcated hinge arm between an initial position and an engaged position, wherein in the engaged position the translation member biases an anterior end of the first bifurcated hinge arm.

18. The expandable bi-dimensional intervertebral implant of claim 17, wherein in the engaged position, a posterior end of the expandable bi-dimensional intervertebral implant has a first height and an anterior end of the expandable bi-dimensional intervertebral implant has a second height greater than the first height.

19. The expandable bi-dimensional intervertebral implant of claim 17, wherein in the engaged position, the translation member splays first and second bifurcated hinge arms.

20. An expandable bi-dimensional intervertebral implant comprising:
a first hinge arm;
a second hinge arm hingedly connected to a mid-portion of the first hinge arm about its mid-portion, and wherein the second hinge arm is movable between a primary position and a secondary position relative to the first hinge arm; and
a translation member movable relative to the first hinge arm and the second hinge arm between an initial position and an engaged position, wherein in the engaged position, the translation member biases an anterior end of the first hinge arm to move from a first position to a second position and biases the second hinge arm to move between a first position and a second position.

* * * * *